(12) United States Patent
Zheng et al.

(10) Patent No.: US 9,006,506 B2
(45) Date of Patent: Apr. 14, 2015

(54) ALKYLATION PROCESS

(75) Inventors: Xiaobo Zheng, Houston, TX (US); John Di-Yi Ou, Houston, TX (US); Mark P. Hagemeister, Houston, TX (US); Jon E. R. Stanat, Westhampton Beach, NY (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 30 days.

(21) Appl. No.: 13/618,211

(22) Filed: Sep. 14, 2012

(65) Prior Publication Data

US 2013/0253245 A1    Sep. 26, 2013

Related U.S. Application Data

(60) Provisional application No. 61/544,491, filed on Oct. 7, 2011.

(51) Int. Cl.
C07C 2/86        (2006.01)

(52) U.S. Cl.
CPC ............... C07C 2/865 (2013.01); C07C 2/864 (2013.01)

(58) Field of Classification Search
USPC ........................................................ 585/467
See application file for complete search history.

(56) References Cited

U.S. PATENT DOCUMENTS

| 5,043,502 | A | 8/1991 | Martindale et al. |
| 6,423,879 | B1 | 7/2002 | Brown et al. |
| 6,504,072 | B1 | 1/2003 | Brown et al. |
| 2010/0040517 | A1 | 2/2010 | Brown et al. |
| 2010/0261941 | A1* | 10/2010 | Hagemeister et al. ........ 585/470 |
| 2011/0092755 | A1* | 4/2011 | Lattner et al. ................ 585/401 |
| 2011/0092756 | A1* | 4/2011 | Lattner et al. ................ 585/446 |
| 2011/0190559 | A1 | 8/2011 | Blessing et al. |

FOREIGN PATENT DOCUMENTS

| EP | 1995218 A1 * | 11/2008 |
| WO | 99/38823 | 8/1999 |

OTHER PUBLICATIONS

U.S. Appl. No. 13/487,651, filed Jun. 4, 2012, Zheng et al.

* cited by examiner

*Primary Examiner* — In Suk Bullock
*Assistant Examiner* — Youngsul Jeong (57) ABSTRACT

The invention relates to the production of paraxylene by an alkylation process that also produces oxygenates. The process is controlled to utilize recycle to minimize said oxygenates.

6 Claims, 6 Drawing Sheets

ALKYLATION PROCESS

PRIORITY CLAIM

This application claims the benefit of Provisional Application No. 61/544,491, filed Oct. 7, 2011, the disclosure of which is incorporated by reference in its entirety.

FIELD OF THE INVENTION

The invention relates to the production of paraxylene by alkylation of benzene and/or toluene with methanol.

BACKGROUND OF THE INVENTION

Paraxylene (also "p-xylene" or "PX") is generally considered the most important of C8 aromatic isomers, being used as an intermediate or starting material for such diverse end uses as synthetic fibers and bottle plastic. Paraxylene is typically obtained from a C8 aromatic hydrocarbon mixture derived from reformate by processes including aromatic extraction and fractional distillation. However, such processes involve high operational costs and result in only limited yields. Increasing selectivity to paraxylene and other operational improvements, especially in the area of separation of paraxylene from other C8 isomers and impurities, is the focus of intense research.

Selectivities to para-xylene in excess of 90 wt % (based on total C8 aromatic product) have been reported by reacting toluene with methanol in the presence of a catalyst comprising a porous crystalline material, preferably a medium-pore zeolite and particularly ZSM-5, having a Diffusion Parameter for 2,2 dimethylbutane of about 0.1-15 $sec^{-1}$ when measured at a temperature of 120° C. and a 2,2 dimethylbutane pressure of 60 torr (8 kPa). See in particular U.S. Pat. Nos. 6,423,879 and 6,504,072.

One problem with these processes has only recently been observed, and that is the production of undesirable oxygenate by-products. Such oxygenate by-products include water, alcohols, ethers, ketones, aldehydes, acids, and phenols. Depending on various factors including the boiling point of the oxygenate, these undesirable by-products are either returned to the alkylation reactor in recycle streams or leave the process through one or more product streams.

In particular, the para-rich xylene product stream (i.e., a product stream having paraxylene in greater than equilibrium amounts, which is approximately 24 mol %, relative to the total xylenes present) tends to contain phenol, methyl phenols and dimethyl phenols. As a result, when the paraxylene is recovered from this product stream, generally by crystallization or by adsorption, the residual para-depleted xylene fraction (i.e., a lower amount of paraxylene than equilibrium amounts, relative to total xylenes) typically contains from ten to several hundred ppmw of phenolic impurities. These impurities limit the value of the para-depleted xylene fraction and generally mean that the fraction can only be used as a blending stream for automotive gasoline.

WO99/38823 teaches a reactive distillation process for the production of xylenes by contacting toluene with a methylating agent. Dimethylether (DME) and unreacted methanol are recycled "to extinction" back to the reactive distillation column. Since it is known that both DME and methanol are useful alkylating agents in this reaction, this solution, at least in hindsight, is not surprising. Reactive distillation systems, however, have numerous drawbacks, particularly in that they are not generally commercially feasible.

One recent improvement in the alkylation of aromatic hydrocarbons with methanol is U.S. Patent Publication 2010-0261941, which is directed to a process using crystallization technology to purify paraxylene from a mixture of large concentrations of C8 aromatics and also small concentrations of oxygenated species.

More recently, a process has been developed whereby the concentration of phenolic impurities in a xylene stream produced by alkylation of benzene and/or toluene with methanol can be reduced to trace levels, e.g., below 0.1 ppmw, by one or more washing treatments with an aqueous solution of a base. The resultant treated xylene stream, if necessary after water washing to remove any phenate-containing solution, can then be recycled to the xylene splitter to generate additional paraxylene or can be used as a solvent. See U.S. patent application Ser. No. 13/487,651.

However, the above solutions do not solve the entirety of problems associated with the presence of oxygenates in the product stream, particularly the presence of phenol. By way of example, there still remains the problem of the presence of oxygenates (other than alkylating agents in the desired reaction) in the unreacted methanol and benzene and/or toluene product stream, as well as water, any of which, if recycled can cause problems in the reactor system, such as catalyst deactivation due to fast coke formation. In addition, there are many other species of oxygenates present in the product stream of the alkylation reactor besides phenolic species. Separation of these oxygenates is costly and difficult. Accordingly, it would be highly beneficial if oxygenates, other than the alkylating agents DME and methanol, could be eliminated or minimized to take better advantage of the para-selectivity of the alkylation of aromatic species with methanol.

The present inventors have surprisingly discovered after careful study that under appropriate conditions such oxygenates will be converted in the reactor without build-up and catalyst performance is not affected by the recycled oxygenates.

SUMMARY OF THE INVENTION

The invention concerns the control of a reactor system for the production of paraxylene by alkylation wherein oxygenates are co-produced, in part by controlling the recycle of unreacted components and/or reaction products so that the steady-state output of oxygenates from the reactor is less than or equal to the input of oxygenates into the reactor.

The invention is directed to a process for the alkylation of benzene and/or toluene with methanol and/or dimethylether (DME) to produce paraxylene, preferably in high selectivity, such as more than 95 mol % based on total xylenes, said process including contacting a feed comprising benzene and/or toluene, methanol and/or dimethylether (DME), and water, with a catalyst comprising a molecular sieve in a reactor wherein reactor conditions are effective to produce a product comprising paraxylene, other C8 aromatic hydrocarbons, co-produced oxygenates, C9+ aromatic hydrocarbons, non-aromatic hydrocarbons including light gases, and unreacted components including the alkylation agent (methanol and/or DME), water, benzene and/or toluene, the improvement comprising:

(a) determining the amount of at least one co-produced oxygenate in said product;

(b) separating said product into separate streams including: (i) one or more streams comprising said unreacted components and co-produced oxygenates; (ii) at least one stream comprising paraxylene; (iii) at least one stream comprising C9+ aromatics, if present; (iv) at least one stream comprising light gases, if present;

(c) recycling at least one stream selected from (i) whereby said at least one stream combines as recycle with said feed;

(d) determining the amount of said at least one oxygenate in said feed, including said recycle;

(e) controlling reactor conditions, step (b) and step (c) so that the amount determined in step (a) is less than or equal to the amount determined in step (d).

In embodiments, at least one of the streams selected from (ii), (iii) and (iv) is not recycled.

It will be understood that the "determining" steps may, independently, be replaced by "predetermined"; likewise it will also be understood that the "amount" may be any indicia of quantity such as concentration of oxygenates; furthermore it will be understood that step (e) does not require that any conditions be changed and that the variables, such as residence time and the like may be allowed to vary around a set point or may be allowed to occur within a set range, and the like, all of which will be discussed in detail below.

It is an object of the invention to avoid problems associated with the presence of oxygenate by-products, particularly with oxygenate by-products other than alkylating agents DME and/or methanol, in the product stream of the process for the production of paraxylene by alkylation of benzene and/or toluene with methanol. The terms "by-products" and "co-products" are used synonymously herein to indicate a species produced in the alkylation reaction.

It is another object of the invention to provide a process which at least in part is capable of converting recycled oxygenate, without using expensive oxygenate separation techniques and equipment such as extraction, adsorption, crystallization, and the like.

It is still another object of the invention to provide a reaction system, other than a catalytic distillation system, for the production of paraxylene selectively while avoiding at least some of the negative consequences of the co-production of oxygenate impurities, particularly phenol.

These and other objects, features, and advantages will become apparent as reference is made to the following detailed description, preferred embodiments, examples, and appended claims.

DETAILED DESCRIPTION

According to the invention, the product stream of a reactor for the alkylation of benzene and/or toluene with methanol and/or dimethylether (DME) in the presence of a molecular sieve catalyst, which contains oxygenates (other than methanol and/or DME) generated in said reactor, is separated into various streams and recycle streams are selected to avoid oxygenate build-up in the reactor system. It is a surprising discovery that, in embodiments, the oxygenates in the recycle streams of the unreacted components do not need to be separated out provided the total oxygenate output of the reactor, with respect to each oxygenate, is less than the total oxygenate input into the reactor.

In a more preferred embodiment, it is the concentration of phenol which is determined (or predetermined) in steps (a) and (d) of the following preferred method:

(a) determining the amount of at least one co-produced oxygenate in said product;

(b) separating said product into separate streams including: (i) one or more streams comprising said unreacted components and co-produced oxygenates; (ii) at least one stream comprising paraxylene; (iii) at least one stream comprising C9+ aromatics, if present; (iv) at least one stream comprising light gases, if present;

(c) recycling at least one stream selected from (i) whereby said at least one stream combines as recycle with said feed;

(d) determining the amount of said at least one oxygenate in said feed, including said recycle; and (e) controlling reactor conditions, step (b) and step (c) so that the amount determined in step (a) is less than or equal to the amount determined in step (d).

The present inventors have determined that multiple species of oxygenates are present in the product stream described above, including alcohols, ketones, ethers, aldehydes, acids, and phenols. The concentrations of oxygenates in both the hydrocarbon phase and the aqueous phase of the product streams range from 1 ppm to 3000 ppm using fresh toluene and methanol as feed on a once-through basis. Separating the oxygenate species from recycle streams (of unreacted starting material), product streams (having stringent specifications of impurities for downstream processing), and waste streams (the composition of which is highly regulated), is difficult and expensive.

Figure 1:
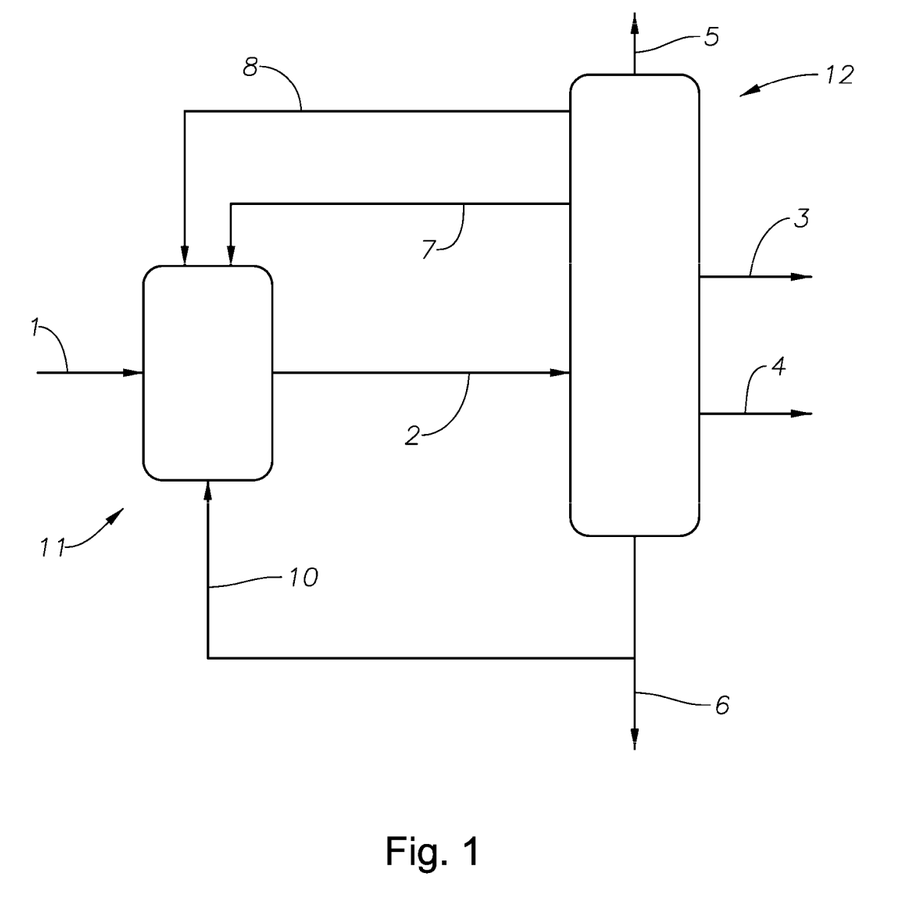
FIG. 1 is a schematic illustrating a system according to the present invention.

Accordingly, species other than phenol may be determined, or the concentration (or some indicia thereof) of phenol and one or more other co-produced oxygenate species may be determined A reactor system according to the present invention is illustrated schematically in FIG. 1. In FIG. 1, alkylation reactor 11 is fed via conduit 1 with reactants methanol, benzene and/or toluene, and water. The reactants may be supplied each separately but preferably as illustrated in the figure as a mixture. The reactor 11 is a fixed bed or fluid bed reactor that contains catalyst, preferably a molecular sieve, to catalyze the reaction of benzene and/or toluene and methanol to paraxylene in high selectivity. The reaction per se and the details of reactor 11 per se are not a subject of the present invention but have been described in the prior art, such as discussed in the Background. The product stream 2, comprising xylenes, preferably having paraxylene present in the amount of at least 90 mol %, based on the xylenes present in said product stream 2, and also unreacted methanol, benzene and/or toluene, water, and numerous oxygenates, is fed to product separation apparatus 12, which is typically one or more fractionation columns and/or liquid-liquid separators and the like, wherein the product stream 2 is separated into a xylene fraction 3, C9+ aromatics (heavies) stream 4, light gas stream 5, waste water stream 6 (which can be separated into a recycle stream 10 returning to reactor 11) benzene and/or toluene stream 7, and methanol stream 8. All these streams from the product separation section 12 contain oxygenates. It should be noted that separation section 12 typically will comprise multiple liquid-liquid separators and multiple fractionation columns, such as two liquid-liquid separators and 3 fractionation columns.

Three streams are shown to be recycled—methanol recycle 8, benzene/toluene recycle 7, and water recycle 10 off of stream 6 are advantageously directly sent back to the reactor 11 without separating out the oxygenates. Under appropriate conditions, the oxygenates are demonstrated to convert in the reactor, at least to the extent that there is no oxygenate build up in the system.

The present inventors have discovered that as long as the oxygenate concentrations in the reactor reach above their equilibrium concentrations, the oxygenates convert and further build-up of oxygenates is prevented. Thus, at or above the equilibrium concentration of each individual oxygenate, the output of the reactor of that oxygenate is less than or equal to the input of each individual oxygenate. At such conditions, the reactor should operate at a steady state or near-steady state, and thus problem-free, at least in regard to problems attributable to oxygenate build-up.

The remaining of the oxygenate products leave the process in the other four streams, namely, light gas 5, xylene stream 3, C9+ aromatics ("heavies") 4, and waste water 6.

The oxygenate recycle ratio A %, which is defined as: [(amount of oxygenate recycled back to the reactor)/(total amount of oxygenate in the reactor outlet)]×100. This can be adjusted based on process design and is different for each oxygenate species.

Figure 2:
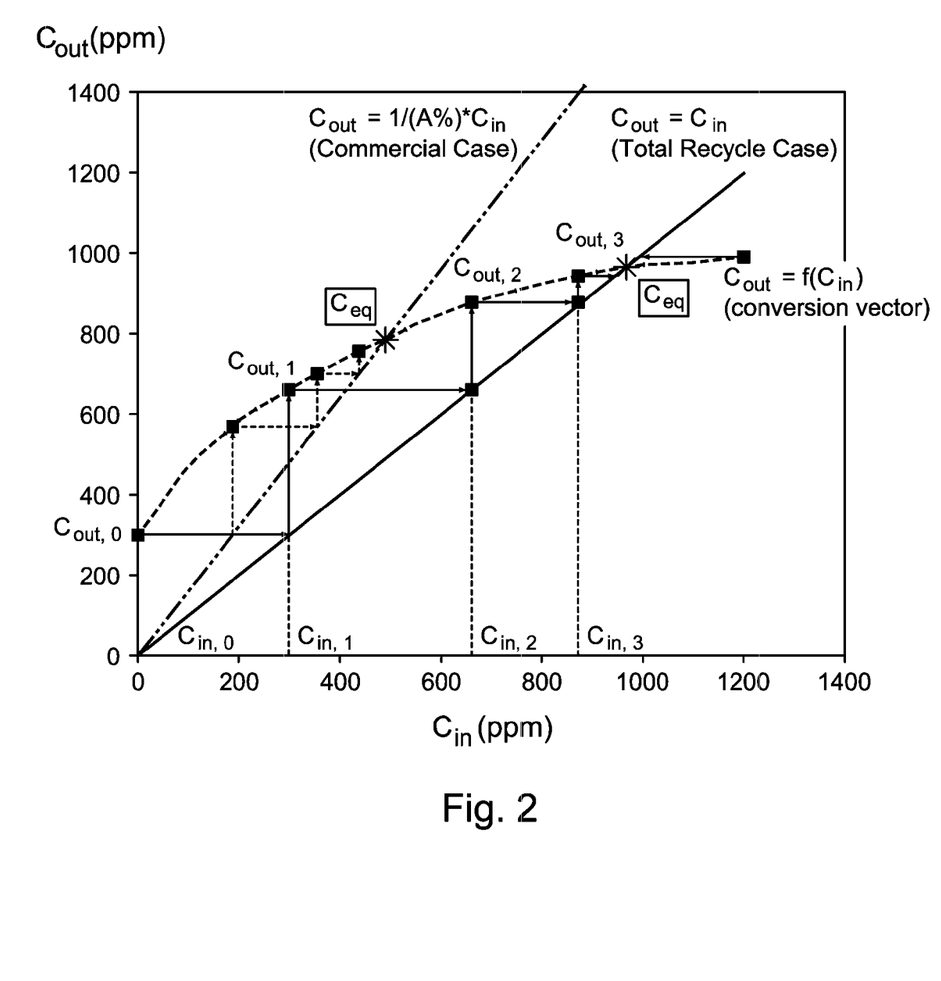
FIG. 2 is an illustration of the concept of oxygenate equilibrium concentration, which is an aspect of the present invention.

FIG. 2 illustrates the concept of oxygenate equilibrium concentration which is the highest concentration of a specific oxygenate in the product. The curve labeled as $C_{out}=f(C_{in})$ represents oxygenate conversion vector that can be measured from the experiments by doping in oxygenates at several different concentrations in the feed and measuring their concentrations at the reactor outlet. The line labeled Total Recycle Case represents oxygenate material balance assuming oxygenates are fully recycled back to the reactor (concentration out=concentration in). The line labeled Commercial Case represents oxygenate material balance in commercial operation, i.e., concentration out=(1/A %)(concentration in), wherein A % is the oxygenate recycle ratio. The cross point between the Conversion Vector curve and the Total Recycle line is oxygenate equilibrium concentrations under total recycle case and the cross point between the Commercial Case line and the Conversion Vector curve represents oxygenate equilibrium concentrations under commercial operation case.

While oxygenate concentration in the reactor feed is lower than its equilibrium concentration, it is in "net production" mode and its concentration continues to increase until it reaches its equilibrium concentration. While oxygenate concentration in the reactor feed is higher than its equilibrium concentration, it is in "net conversion" mode and its concentration continues to decrease until it reaches its equilibrium concentration. Therefore, oxygenate equilibrium concentration is the highest oxygenate concentration to be expected in steady state of the oxygenate recycled.

The equilibrium concentration under the full recycle case (100% of the oxygenate at the reactor product effluent is recycled back to the reactor inlet) is always higher than the equilibrium concentration in commercial operation. Since oxygenate recycle ratio depends on process design, A % may vary from one process design to the other. The equilibrium concentration under full recycle may be used as the "worst case scenario" to estimate the highest oxygenate concentration expected in any proposed recycle scheme.

The following examples should be taken as representative of the present invention and should not be interpreted as limiting thereof. One of ordinary skill in the art in possession of the present disclosure will recognize that many alternative variations of the following are possible.

The catalyst used in each example was a ZSM-5 zeolite steam-treated at 1035° C. and then 1055° C. The $SiO_2/Al_2O_3$ was 450. The catalyst tests were done in a down flow reactor. The reactor temperature was 1100° F. (approximately 593° C.) and the reactor pressure was 20 psig. The feeds used in this example were HPLC grade methanol, toluene and water, purchased from Aldrich.

Example 1

Oxygenate Equilibrium Concentrations

Figure 3:
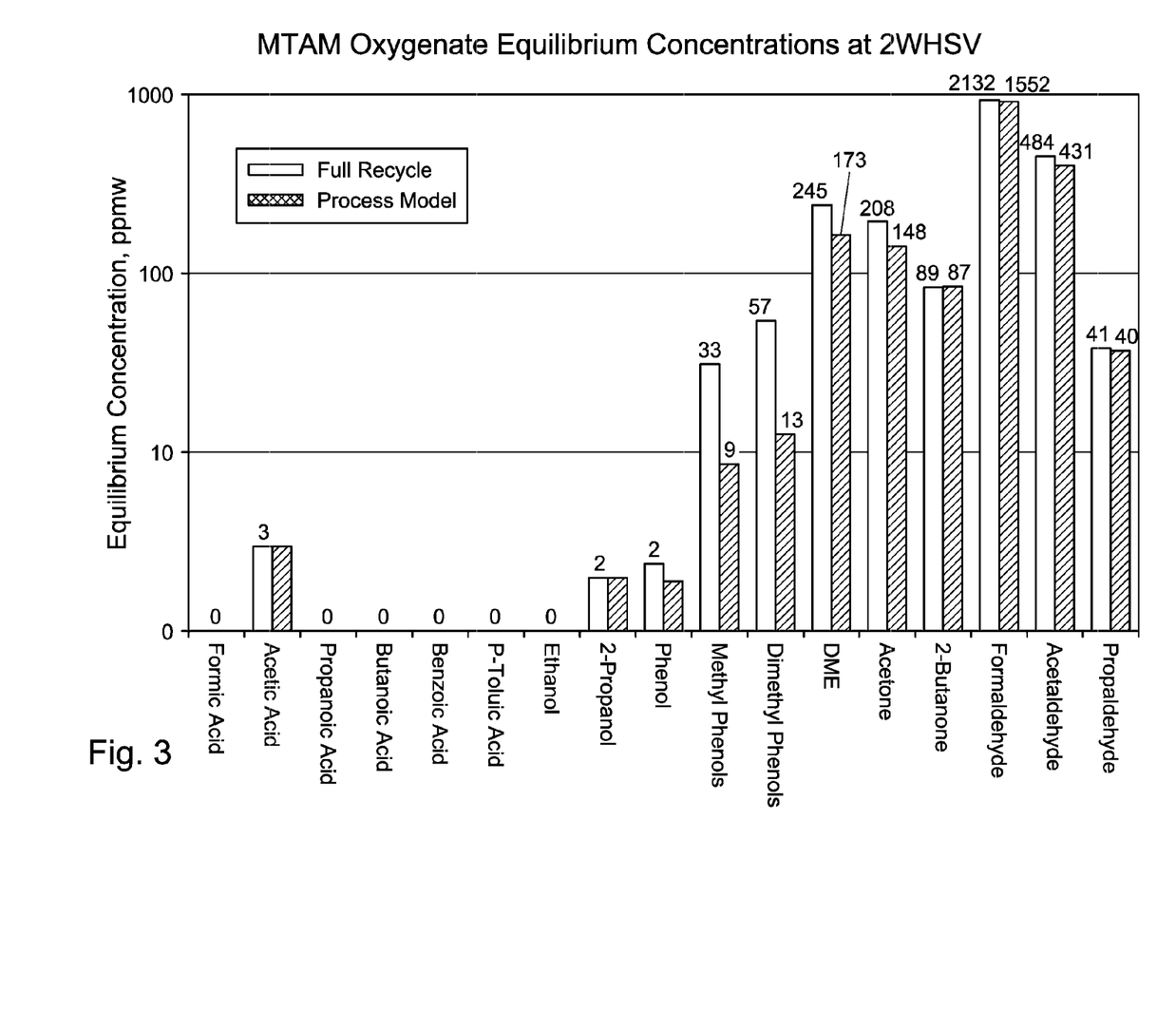
FIGS. 3-6 show results of specific examples according to the invention.

The alkylation reaction in a reactor system according to FIG. 1 is operated at a WHSV (weight hourly space velocity) of 2. FIG. 3 illustrates a plot of oxygenate equilibrium concentrations ("process model") as compared with "full recycle", which is the amount of the specific oxygenate exiting the reactor using completely fresh feed and no recycle.

Example 2

Oxygenate Conversion at Standard Conditions

Figure 4:
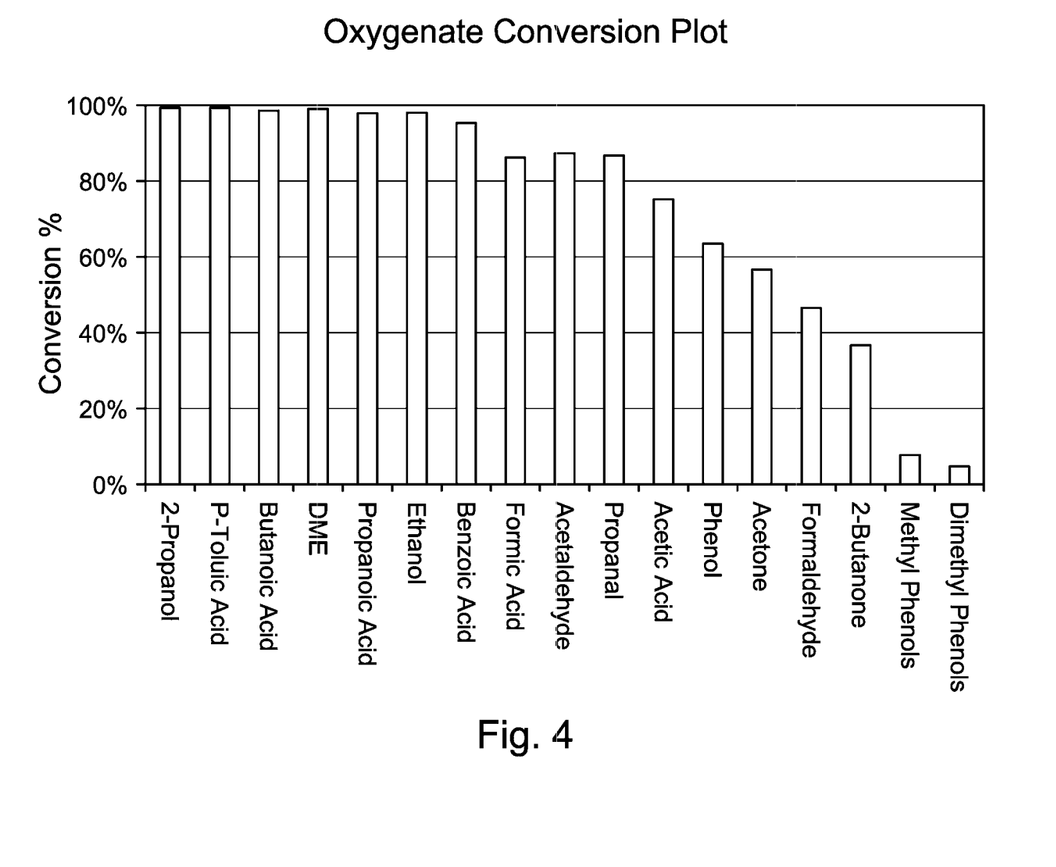

FIG. 4 is a plot of oxygenate conversion at their feed concentrations shown in Table 1, below. At hydrocarbon WHSV=2, $H_2O/HC=2$ (mol:mol), all oxygenate concentrations in the feed are higher than their equilibrium concentrations and they all showed positive conversion.

TABLE I

| Oxygenates | Feed Blend Concentration, ppmw | Equilibrium Concentration, ppmw |
| --- | --- | --- |
| Formaldehyde | 2500 | 2132 |
| Acetaldehyde | 2000 | 484 |
| Propaldehyde | 200 | 41 |
| Acetone | 2000 | 208 |
| 2-Butanone | 200 | 89 |
| DME | 1000 | 245 |
| Ethano | 200 | 0 |
| 2-Propanol | 200 | 2 |
| Formic acid | 200 | 0 |
| Acetic acid | 200 | 3 |
| Propanoic acid | 200 | 0 |
| Butanoic acid | 200 | 0 |
| Benzoic acid | 200 | 0 |
| Tolui acid | 200 | 0 |
| Phenol | 200 | 2 |
| M-pheno | 200 | 33 |
| DM-Phenol | 200 | 57. |

Example 3

Reactor Condition Impacts on MTAM Oxygenate Conversion

Figure 5:
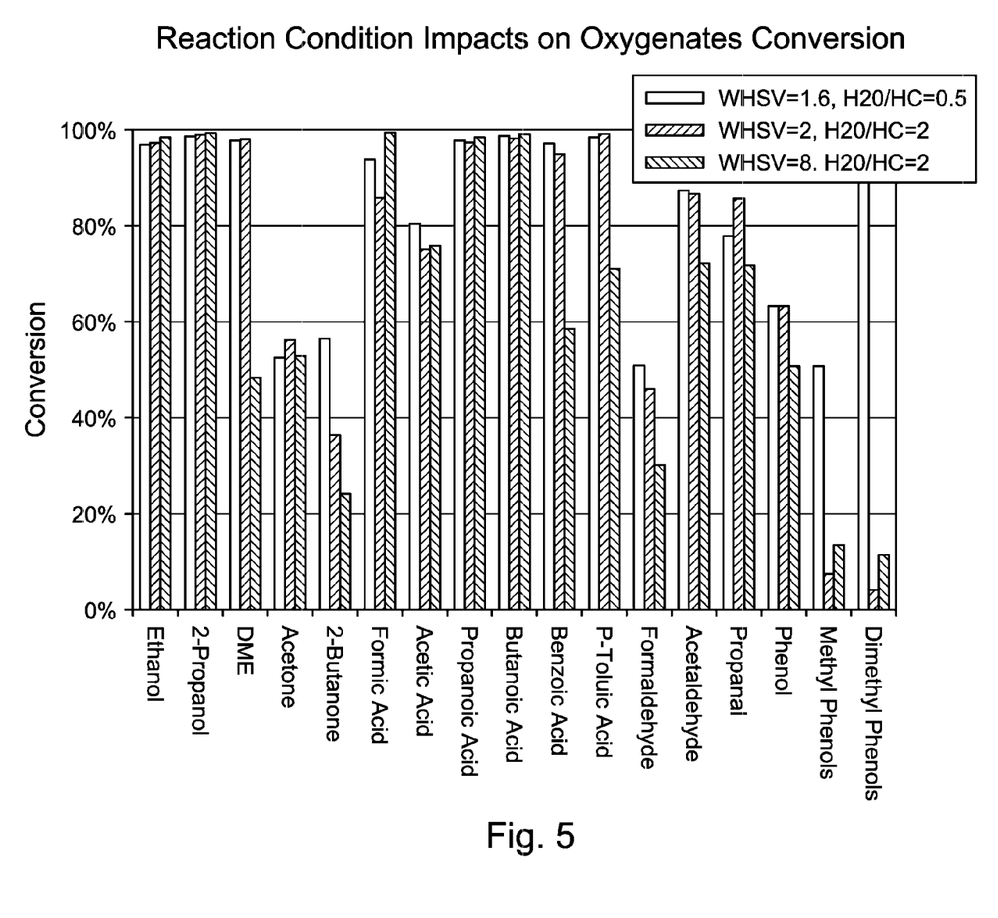

In this example, tests were conducted at three different conditions, HC (hydrocarbon) WHSV=1.6 and $H_2O/HC=0.5$, HC WHSV=2 and $H_2O/HC=2$, and HC WHSV=8 and $H_2O/HC=2$. The oxygenate concentrations in the feed are the same as in Example 3. The residence time ranks in the order of WHSV=1.6 and $H_2O/HC=0.5$>WHSV=2 and $H_2O/HC=2$>WHSV=8 and $H_2O/HC=2$. The results shown in FIG. 5 suggest that oxygenate conversion is a function of their residence time. Oxygenate conversion are high for process conditions with long residence time and low for process conditions with short residence time.

Example 4

Oxygenate Impact on Catalyst Performance

Figure 6:
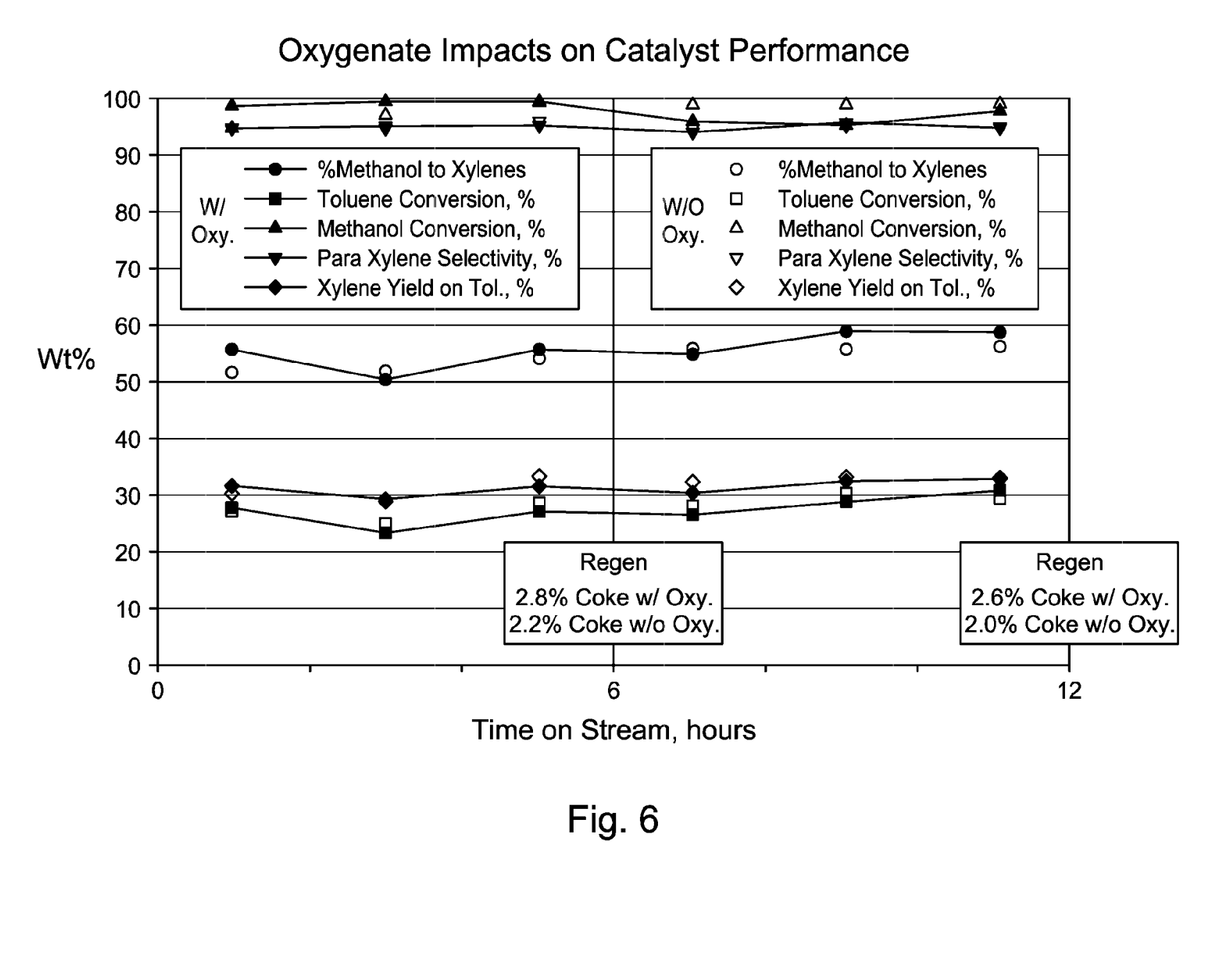

In this example, tests were conducted at WHSV=2 and $H_2O/HC=2$ with and without oxygenate in the feed. The oxygenate concentration in the feed is shown in Table 1. The results in FIG. 6 suggests that oxygenate doped in the feed with concentration much higher than its equilibrium concentration does not impact catalyst performance, i.e., similar toluene/methanol conversion, para-xylene selectivity, and methanol utilization (methanol converted to para-xylene/total methanol converted) are observed. The only difference observed is coke on catalyst amount at the end of each 6 hour test. Coke on catalyst amount higher for oxygenate containing feed than feed without oxygenate. This difference can be handled fairly easily during catalyst regeneration.

It will be recognized by one of skill in the art that one or more process parameters can be attenuated in order to insure the proper concentrations of the oxygenates satisfies the conditions with respect to input to and output from the reactor. Such conditions include but are not limited to alkylation reactor temperature, pressure, toluene and/or benzene and/or methanol and/or water feed rate(s), and recycle rate of the respective recycled streams, and the like.

Suitable catalysts, reactors, and reactor conditions are per se known in the art. Particularly preferred catalysts include a steamed, phosphorus modified ZSM-5 with a clay binder. Reactors and reactor conditions are preferably those described in U.S. Pat. Nos. 4,002,698; 4,356,338; 4,423,266; 5,675,047; 5,804,690; 5,939,597; 6,028,238; 6,046,372; 6,048,816; 6,156,949; 6,423,879; 6,504,072; 6,506,954; 6,538,167; and 6,642,426. Preferably the addition of the alkylating agent is by staged injection into a reactor having similarly staged baffles. Preferably the reactor temperature is at 400° C. or above 400° C. Suitable reaction conditions may be readily determined by one of ordinary skill in the art in possession of the present disclosure and by way of example may include the following ranges: (a) Temperature—about 500° to about 700° C., and preferably between about 500° to about 600° C.; (b) Pressure—about 1 atmosphere to about 1000 psig (about 100 to about 7000 kPa), and preferably about 10 psig to about 200 psig; (c) moles toluene/moles methanol (in the reactor charge)—at least about 0.2, and preferably from about 0.2 to about 20; and (d) a weight hourly space velocity ("WHSV") for total hydrocarbon feed to the reactor(s) of about 0.2 to about 1000, preferably about 0.5 to about 500 for the aromatic reactant, and about 0.01 to about 100 for the combined alkylating reagent stage flows, based on total catalyst in the reactor(s).

The terms "selective for paraxylene", "paraxylene selective", and the like, means that paraxylene is produced in amounts greater than is present in a mixture of xylene isomers at thermodynamic equilibrium, which at ordinary processing temperatures is about 24 mol %.

The surprising discovery of the present invention avoids costly separation of oxygenates from recycle downstream of the alkylation reactor. Nevertheless, in conjunction with the above-described invention, there may also be employed, in embodiments, separation techniques downstream of reactor such as crystallization, adsorption, extraction, azeotropic distillation, and the like. Removal of polar compounds, with widely different properties (such as between organic acids, and phenols for instance) and in low concentrations is very difficult, in part because these oxygenates form azeotropes with xylenes and other aromatic streams, thus making conventional distillation to remove oxygenates from xylene streams impractical if not impossible. However, azeotropic distillation can be a rather effective way to remove trace quantities of polar compounds such as oxygenates from aromatic-containing streams such as xylenes separated downstream of the alkylation reactor. A ternary azeotrope is formed in a distillation column by feeding an aqueous mixture of methanol and water, along with the hydrocarbon-bearing xylenes stream (which happens to contain the various types of possible oxygenates). The azeotrope thus formed and condensed in the overhead causes xylenes, methanol, and a little water to accumulate in the distillation column's overhead accumulator, where the xylenes can be effectively separated by gravity settling from the aqueous stream. The methanol (with some water) stream is then recycled back to the column.

The azeotropic distillation process is particularly well suited for the present invention because, among other things, (a) methanol and water are easily available; (b) xylenes as aromatics are compatible with the azeotropic process; and (c) the energy supplied to the column, which is needed for vaporization of methanol and xylenes, is not excessive due to their advantageously low relative heats of vaporization. Water, which has a high heat of condensation, is only slightly condensed in the overhead accumulator, the great majority rejected to the column bottoms where oxygenates are nearly 100% recovered. Thus, the required duty to vaporize methanol and the xylenes is not substantial in terms of operating costs. In embodiments the alkylation reaction step in the present invention is a net exporter of heat at moderate to high pressures for the reboiler heat requirements, thus providing additional energy for said reboiler via steam export from the reaction system to the azeotropic distillation column. Note that the above-mentioned azeotropic distillation is generic enough to be used for other aromatics processes with polar contaminants, as long as the physical properties are acceptable to form an azeotrope between water and methanol (or other alcohol used), to ensure no desired aromatic hydrocarbons would exit in the column bottoms stream as normal (non-azeotropic) distillation would indicate.

The azeotropic distillation process has been tested in simulations using many different types of oxygenates (ketones, aldehydes, organic acids, phenols, ethers, etc.) which have normal boiling points both close and far away from paraxylene. Another advantage of this azeotropic distillation process is that the water and methanol feed rates can be adjusted to the column to account for some difficult-to-remove oxygenates (more entrainer) and less difficult (less entrainer), as well as the water to methanol ratio itself. Yet an additional advantage of this azeotropic distillation process compared to alternatives is that in the chemical industry, in the vast majority of cases, azeotropes in distillation and other systems either don't exist due to physical property reasons or have been intentionally designed out of the process via changes in the process which adjust properties of streams such as pH, or particular compositional constraints for various components which avoids the two common types of azeotropes: minimum boiling and maximum boiling.

When azeotropes do exist in the chemical industry, they are almost universally detrimental to a plant's operation because it becomes theoretically impossible in many cases to separate two or three components which comprise an azeotropic binary or ternary because technically in that situation, without process operational or unit modification(s), no amount of reflux rate or tray number increases will ever provide the separation of the given azeotrope. Conversely, the azeotropic process described above intentionally drives xylenes into the overhead stream via the three phase (water-methanol-xylenes), while water is rejected to the bottoms stream. In any normal distillation process, the xylenes would be substantially rejected to the bottoms stream due to physical properties like relative volatility and boiling points of xylenes, which would eliminate the possibility of effectively removing xylenes from the oxygenates.

The azeotropic distillation tower can be of rather limited height due to the highly effective ability for the azeotrope to reject oxygenates to a water stream, and can utilize inexpensive carbon steel, and requires a relatively small associated accumulator. Heat is applied to the column with available medium or low pressure heat such as steam through a reboiler. Note that very little water is vaporized in this process, which is important from an energy standpoint due to a significant water requirement coupled with a high latent heat value for water. Instead, energy is needed only to vaporize the hydrocarbon (xylenes) stream and a limited amount of methanol, which both have relatively low heats of vaporization, thus keeping total energy requirements for vaporization to reasonably low values and thus cost. An accumulator in the overhead stream of the column, after suitable condensing in an overhead condenser, will begin to fill with a mixture of xylenes, a little water, and a weight percent concentration of methanol, depending on final design and feed impurities. The accumulator is advantageously a baffled two liquid phase type accumulator per se known in the art. The xylenes (with a little aqueous mixture) will be gravity settled and removed from the top of the settler, while the bottom of the settler (water boot) will recycle the methanol-rich aqueous stream back to the column as reflux. The reflux reduces the need and cost of methanol in terms of operating cost. The xylenes mixture, which then contains no free water and is saturated at approximately 1000-3000 wppm water (depending on temperature), can be dried via (a) nitrogen stripping or (b) dryer beds, depending on economics. The recovery of essentially every possible oxygenate that could appear in paraxylene can be reduced by over 90%, in most cases >99% wt. The oxygenate and water free xylenes can then be sent to further distillation, as normal for aromatics processes, to remove benzene, toluene, xylenes, and C9+ heavies streams.

Again, however, it is an advantage of the present invention that appropriate recycling avoids oxygenate separation techniques such as the above mentioned distillation, adsorption, crystallization, and the like, on the recycle streams.

The invention has been described above with reference to numerous embodiments and specific examples. Many variations will suggest themselves to those skilled in this art in light of the above detailed description. Particularly preferred embodiments include:

(I) a process for the production of paraxylene by alkylation of aromatic hydrocarbons with methanol in the presence of at least one molecular sieve comprising:

(a) providing a feed comprising an alkylating agent selected from methanol, dimethylether, and mixtures thereof, and an aromatic hydrocarbon selected from benzene, toluene, and mixtures thereof, to a reactor;

(b) contacting in said reactor said alkylating agent and aromatic hydrocarbon in the presence of at least one molecular sieve and under conditions suitable for the production of paraxylene selectively;

(c) obtaining a stream comprising (i) paraxylene, (ii) unreacted alkylating agent, (iii) unreacted aromatic hydrocarbon, (iv) water, and at least one oxygenate (other than water and said alkylating agent(s)) co-produced with paraxylene in step (a);

(d) separating (i), (ii), (iii), and (iv) into plural streams, each containing said at least one oxygenate; and (e) recycling at least one of said plural streams comprising at least one of (ii), (iii), and (iv) to step (a) without a step of separation of said at least one oxygenate from said at least one plural streams;

(II) a process for the production of paraxylene by alkylation of aromatic hydrocarbons with methanol in the presence of at least one molecular sieve comprising:

(a) providing a feed comprising methanol and/or dimethylether, and benzene and/or toluene;

(b) contacting said feed in an alkylation reactor in the presence of at least one molecular sieve and under conditions suitable for the production of paraxylene selectively;

(c) obtaining a stream comprising (i) paraxylene, (ii) methanol and/or dimethylether, (iii) benzene and/or toluene, (iv) water, and at least one oxygenate (other than methanol, dimethylether, and water) co-produced with paraxylene in step (a);

(d) separating (i), (ii), (iii), and (iv) into plural streams, each containing said at least one oxygenate; and (e) recycling at least one of said plural streams comprising at least one of (ii), (iii), and (iv) to said feed in step (a), with the proviso that the concentration of said at least one oxygenate co-produced with paraxylene provided as feed in step (a) is equal to or greater than the concentration of each oxygenate in step (c);

(III) a process for the production of paraxylene by alkylation of aromatic hydrocarbons with methanol in the presence of at least one molecular sieve comprising:

(a) providing a feed comprising methanol, benzene and/or toluene;

(b) contacting said feed in an alkylation reactor in the presence of at least one molecular sieve and under conditions suitable for the production of paraxylene selectively;

(c) obtaining a stream comprising (i) paraxylene, (ii) methanol, (iii) benzene and/or toluene, (iv) water, and at least one oxygenate (other than methanol and water) co-produced with paraxylene in step (a);

(d) separating (i), (ii), (iii), and (iv) into plural streams, each containing said at least one oxygenate; and (e) recycling at least one of said plural streams comprising at least one of (ii), (iii), and (iv) to said feed in step (a), with the proviso that the concentration of said at least one oxygenate co-produced with paraxylene provided as feed in step (a) is equal to or greater than the concentration of each oxygenate in step (c);

(IV) a process for the production of paraxylene by alkylation of aromatic hydrocarbons with methanol in the presence of at least one molecular sieve comprising:

(a) providing a feed comprising dimethylether, benzene and/or toluene;

(b) contacting said feed in an alkylation reactor in the presence of at least one molecular sieve and under conditions suitable for the production of paraxylene selectively;

(c) obtaining a stream comprising (i) paraxylene, (ii) dimethylether, (iii) benzene and/or toluene, (iv) water, and at least one oxygenate (other than dimethylether and water) co-produced with paraxylene in step (a);

(d) separating (i), (ii), (iii), and (iv) into plural streams, each containing said at least one oxygenate; and (e) recycling at least one of said plural streams comprising at least one of (ii), (iii), and (iv) to said feed in step (a), with the proviso that the concentration of said at least one oxygenate co-produced with paraxylene provided as feed in step (a) is equal to or greater than the concentration of each oxygenate in step (c);

(V) a process for the alkylation of benzene and/or toluene with methanol to produce paraxylene selectively, including contacting a feed comprising benzene and/or toluene, an alkylating agent selected from methanol, dimethylether, and mixtures thereof, and optionally water, with a catalyst comprising a molecular sieve in a reactor wherein said molecular sieve and reactor conditions are effective to produce a product comprising paraxylene selectively, at least one oxygenate (other than water and said alkylating agent), C9+ aromatic hydrocarbons, light gases, and unreacted components including said alkylating agent, water, benzene and/or toluene, the improvement comprising:

(a) determining the amount of at least one of said oxygenate in said product;

(b) separating said product into separate streams including: (i) one or more streams comprising said unreacted components and said at least one oxygenate; (ii) a stream comprising paraxylene; (iii) a stream comprising C9+ aromatics; (iv) a stream comprising light gases;

(c) recycling at least one stream selected from (i) whereby said at least one stream combines as recycle stream with said feed;

(d) determining the amount of at least one of said at least one oxygenate in said feed, including said recycle; and (e) controlling reactor conditions, and/or at least one of steps (b) and step (c), so that the amount determined in step (a) is less than or equal to the amount determined in step (d).

Modifications of any of the aforementioned preferred embodiments include: a step of determining the concentration of at least one of an oxygenate other than methanol and/or dimethylether produced in said reactor and/or determining the concentration of at least one of an oxygenate other than methanol and/or dimethylether provided to said reactor at a first preselected time and comparing at least one of said concentrations with a predetermined concentration or at least one of said concentrations determined at a second predetermined time, different from said first predetermined time; a step of attenuating at least one process parameter so that the output of at least one oxygenate other than methanol and/or dimethylether produced in said reactor is reduced; and/or a step of attenuating at least one process parameter so that the input of at least one oxygenate other than methanol and/or dimethylether produced in said reactor is increased. It is preferred that the process parameter attenuated is the recycle rate of at least one of the streams recycled to said reactor, and/or at least one parameter of said reactor selected from the group consisting of reactor temperature, reactor pressure, toluene and/or methanol and/or water flow rate(s). It is preferred that the reactor conditions include a temperature of at least 400° C. The phenol in the feed may be determined from time-to-time or continuously, and the decision to do one or the other may also be determined from time-to-time or continuously by operator choice or computer program, or a combination thereof.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. A process for the production of paraxylene by alkylation of aromatic hydrocarbons with methanol in the presence of at least one molecular sieve comprising:

(a) providing a feed comprising an alkylating agent selected from methanol, dimethylether, and mixtures thereof, and an aromatic hydrocarbon selected from benzene, toluene, and mixtures thereof, to a reactor;

(b) contacting in said reactor said alkylating agent and aromatic hydrocarbon in the presence of at least one molecular sieve and under effective conditions to produce a product stream comprising paraxylene, unreacted alkylating agent, unreacted aromatic hydrocarbon, water, and at least one oxygenate (other than water and said alkylating agent(s));

(c) separating the product stream into plural streams of (i) paraxylene stream, (ii) unreacted alkylating agent stream, (iii) unreacted aromatic hydrocarbon stream, and (iv) water stream, wherein each stream contains said at least one oxygenate (other than water and said alkylating agent(s));

(d) recycling at least one of said plural streams comprising at least one of (ii), (iii), and (iv) to step (a) without a step of separation of said at least one oxygenate from said at least one of said plural streams; and (e) attenuating at least one process parameter so that the amount of said at least one oxygenate in the product stream is less than or equal to the amount of at least one oxygenate in said feed, wherein said process parameter is at least one parameter of said reactor selected from the group consisting of recycle rate of at least one of the streams recycled to said reactor, reactor temperature, reactor pressure, toluene flow rate to said reactor, methanol flow rate to said reactor, and water flow rate to said reactor.

2. The process of claim 1, including a step of determining a concentration of at least one of an oxygenate other than methanol and/or dimethylether produced in said reactor and/or determining a concentration of at least one of an oxygenate other than methanol and/or dimethylether provided to said reactor at a first preselected time and comparing at least one of said concentrations with a predetermined concentration or at least one of said concentrations determined at a second predetermined time, different from said first predetermined time.

3. The process of claim 1, wherein said effective conditions include a temperature of at least 400° C.

4. The process of claim 1, wherein a concentration of phenol in the feed and in the product stream is determined from time-to-time.

5. The process of claim 1, wherein a concentration of phenol in the feed and in the product stream is determined continuously.

6. The process of claim 1, including attenuating at least one process parameter so that a recycle rate of phenol is increased or decreased.

* * * * *